US007551959B2

(12) United States Patent
Heil, Jr. et al.

(10) Patent No.: US 7,551,959 B2
(45) Date of Patent: Jun. 23, 2009

(54) CARDIAC RHYTHM MANAGEMENT FOR FETAL, NEONATAL, AND/OR PEDIATRIC PATIENTS

(75) Inventors: Ronald W. Heil, Jr., Roseville, MN (US); Beverly Mains, Minneapolis, MN (US); Christopher P. Knapp, Ham Lake, MN (US); Kyle Hoecke, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 280 days.

(21) Appl. No.: 11/179,121

(22) Filed: Jul. 12, 2005

(65) Prior Publication Data

US 2007/0016276 A1   Jan. 18, 2007

(51) Int. Cl.
*A61N 1/39* (2006.01)
*A61B 5/0448* (2006.01)

(52) U.S. Cl. ........................................................ 607/4
(58) Field of Classification Search ................. 607/119, 607/1–8; 600/511, 376, 300, 304, 313, 338, 600/351, 374, 381, 453
See application file for complete search history.

(56) References Cited

U.S. PATENT DOCUMENTS

| | | | | |
|---|---|---|---|---|
| 4,013,081 A | * | 3/1977 | Kolenik | 607/9 |
| 4,516,584 A | * | 5/1985 | Garcia | 607/119 |
| 4,822,337 A | * | 4/1989 | Newhouse et al. | 604/503 |
| 5,370,627 A | * | 12/1994 | Conway | 604/180 |
| 6,078,839 A | * | 6/2000 | Carson | 607/116 |
| 6,551,285 B1 | * | 4/2003 | Bierman | 604/180 |
| 6,862,475 B1 | * | 3/2005 | Kroll | 607/9 |
| 2002/0082658 A1 | | 6/2002 | Heinrich et al. | |
| 2003/0032998 A1 | * | 2/2003 | Altman | 607/120 |
| 2004/0215301 A1 | | 10/2004 | Lokhoff et al. | |
| 2005/0021093 A1 | | 1/2005 | Brown | |

OTHER PUBLICATIONS

Kohl et al. Fetoscopic and open transumbilical fetal cardiac catheterization in sheep: potential approaches for human fetal cardiac intervention. Circulation. 1997; 95:1048-1053.*
Kohl et al. Transesophageal echocardiography in fetal sheep: a monitoring tool for open and fetoscopic cardiac procedures. Surg Endosc. 1996; 10:820-824.*

(Continued)

*Primary Examiner*—Carl H Layno
*Assistant Examiner*—Jessica Reidel
(74) *Attorney, Agent, or Firm*—Schwegman, Lundberg & Woessner, P.A.

(57) ABSTRACT

A method including inserting an electrode into an umbilical vein, and advancing the electrode through the umbilical vein to a location near or in a heart. In an example, the electrode is inserted into an umbilical vein in utero. In another example, the electrode is inserted into an umbilical vein in a child soon after the child is born. In an example, the electrode is connected to a lead. In an example, a lead is inserted through a catheterized umbilicus.

19 Claims, 12 Drawing Sheets

OTHER PUBLICATIONS

Walkinshaw et al. In utero pacing for fetal congenital heart block. Fetal Diagn Ther. 1994; 9:183-185.*

Kohl T. Fetal echocardiography: new grounds to explore during fetal cardiac intervention. Pediatr Cardiol. 2002; 23:334-346.*

Hanseus et al. Emergency pacing and subsequent permanent pacemaker implantation in a premature infant of 1770 g with a follow-up of 6 years. Pediatr Cardiol. 2000; 21: 470-473.*

Scagliotti et al. Permanent Cardiac Pacemaker Implant in the Fetal Lamb. Pacing Clin Electrophysiol. 1987; 10(6): 1253-1261.*

Ten Harkel et al. Efficacy of an implantable cardioverter-defibrillator in a neonate with LQT3 associated arrhythmias. Europace. 2005; 7: 77-84.*

Kriebel, T. et al. Implantation of an "Extracardiac" Internal Cardioverter Defibrillator in a 6-Month-Old Infant. Zeitschrift fur Kardiologic. 2005; 94: 415-418.*

E. Villain et al. "Artificial Pacing in Neonates With Congenital Complete Atrioventricular Block: Study of 16 Cases" Pediatric Cardiology Department, Necker Hospital (1989) 82: 739-744; English Translation.*

Assad, Renato S., et al., "New lead for in utero pacing for fetal congenital heart block", *The Journal of Thoracic and Cardiovascular Surgery*, vol. 126, No. 1, (Jul. 2003), 300-302.

Berul, Charles I., et al., "Minimally Invasive Cardioverter Defibrillator Implantation for Children", *PACE*, vol. 24, No. 12, (Dec. 2001), 1789-1794.

* cited by examiner

CARDIAC RHYTHM MANAGEMENT FOR FETAL, NEONATAL, AND/OR PEDIATRIC PATIENTS

TECHNICAL FIELD

This patent document pertains generally to cardiac rhythm management systems and methods, and more particularly, but not by way of limitation, to cardiac rhythm management systems and methods for fetal, neonatal, and/or pediatric patients.

BACKGROUND

Antiarrhythmia therapies such as pacing and defibrillation frequently involve delivery of an electric signal to the heart or to anatomy near the heart. Pacing therapies include delivery of a low-energy electrical pulse to the heart. Defibrillation therapies typically include delivery of an electrical energy signal that is strong enough to defibrillate the heart.

A pacer device typically includes a pulse generator and an electrode through which an electrical signal is delivered to the heart. A defibrillator typically includes a pulse generator and two or more electrodes through which an antitachyarrhythmia therapy is delivered. Some devices include both pacing and defibrillation capability. In an example, a medical device includes a lead assembly having at least one electrode that is positionable in, on, and/or around the heart. An antiarrhythmia therapy is delivered using the at least one electrode. In mature patients, a medical device such as a pacer or defibrillator is usually implanted in the thorax, with leads extending from the medical device and into a vein that leads into the heart. A pulse generator is frequently implanted subcutaneously, for example.

In small patients, especially in utero patients, implantation of subcutaneous devices and lead assemblies can be complicated because of the small, fragile, rapidly-growing anatomy of the patient. Improved cardiac rhythm management methods and systems for fetal, neonatal and/or pediatric patients are needed.

SUMMARY

An example method includes inserting an electrode into an umbilical vein, and advancing the electrode through the umbilical vein to a location near or in a heart. In an example, inserting an electrode into an umbilical vein includes inserting the electrode in utero. In an example, inserting an electrode into an umbilical vein includes inserting a lead assembly into the umbilical vein, the lead assembly including the electrode. The method optionally further includes coupling a pulse generator to the lead assembly and coupling the pulse generator to a placenta or the umbilical vein. In another example, the method further includes forming a coil or loop in the lead assembly, the coil or loop accommodating growth of cardiac or venous anatomy. In another example, inserting a lead assembly into the umbilical vein includes inserting the lead assembly through a slip suture sleeve. In another example, the method further includes coating a portion of the lead assembly with an adhesion-preventing drug-eluting coating or covering a portion of the lead assembly with ePTFE. The method optionally further includes delivering a pacing signal or antitachyarrhythmia signal using the electrode. In an example, inserting an electrode into an umbilical vein includes catheterizing an umbilicus after birth or surgically accessing an abdominal region and inserting the electrode into the umbilical vein at a location inside the abdomen.

Another example method includes inserting a first defibrillation electrode into an umbilical vein, and advancing the first defibrillation electrode to a location in or near a heart. In an example, advancing the first defibrillation electrode to a location in or near a heart includes advancing the first defibrillation electrode to a position that is near the heart but not in the heart. The method optionally further includes inserting a second defibrillation electrode in the umbilical vein and advancing the second defibrillation electrode to an intrathoracic position. In an example, advancing the second defibrillation electrode to an intrathoracic position includes advancing the second defibrillation electrode to a location in or near the abdomen. The method optionally further includes delivering an electrical signal using the first defibrillation electrode and the second defibrillation electrode.

In an example, inserting a first defibrillation electrode into an umbilical vein and inserting a second defibrillation electrode in the umbilical vein include inserting a lead assembly into the umbilical vein, the lead assembly including the first defibrillation electrode and the second defibrillation electrode. In another example, advancing the first defibrillation electrode to a location in or near a heart includes advancing the first defibrillation electrode through the heart and into the superior vena cava (SVC). In another example, advancing the defibrillation electrode to a location in or near a heart includes positioning the electrode in the inferior vena cava (IVC). The method optionally includes implanting a pulse generator, coupling the pulse generator to the first defibrillation electrode and second defibrillation electrode, and delivering an electrical signal using the first defibrillation electrode and a second defibrillation electrode. In an example, implanting a pulse generator includes implanting the pulse generator in a left abdominal position. The method optionally includes coupling a lead assembly to the pulse generator and positioning a portion of the lead assembly including the second defibrillation electrode superior to the pulse generator, or in an inferior vena cava (IVC).

Another example method includes delivering an antiarrhythmia therapy using a lead assembly extending through an umbilical vein. In an example, delivering an antiarrhythmia therapy includes delivering the therapy in utero. In another example, the lead assembly includes a first defibrillation electrode and delivering an antiarrhythmia therapy includes delivering an antitachyarrhythmia therapy using the first defibrillation electrode. In another example, delivering an antiarrhythmia therapy using a lead assembly extending through an umbilical vein includes delivering an antiarrhythmia therapy through a catheterized umbilicus after birth. In an example, delivering an antiarrhythmia therapy using a lead assembly extending through an umbilical vein includes delivering the antiarrhythmia therapy through a lead assembly surgically implanted into the umbilical vein through an abdominal incision. In another example, delivering an antiarrhythmia therapy includes delivering the antiarrhythmia therapy using a first electrode on the lead assembly and a second electrode on a second lead assembly extending into the inferior vena cava.

DETAILED DESCRIPTION

Figure 1:
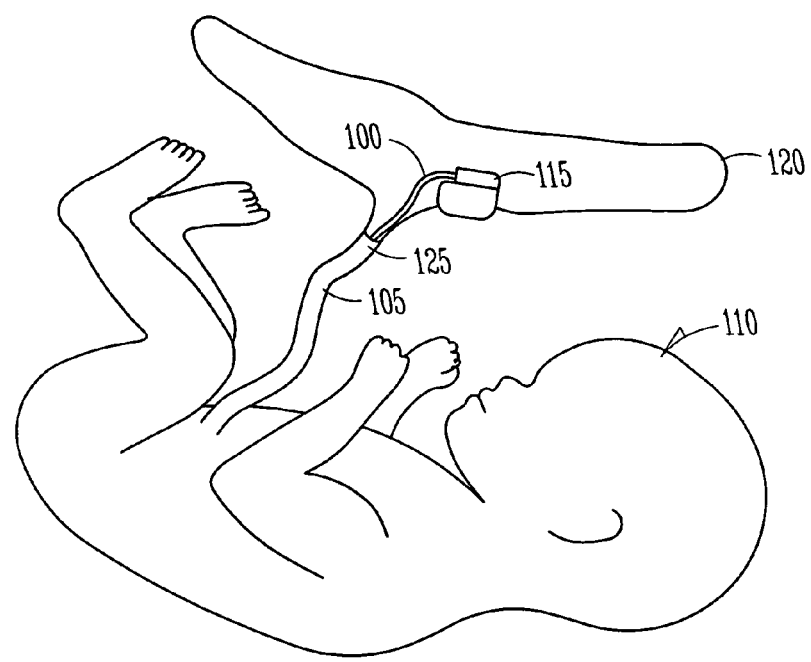
FIG. 1 is an illustration of a fetus, a placenta, a lead assembly inserted into an umbilical cord, and a pulse generator coupled to the lead assembly.

The following detailed description includes references to the accompanying drawings, which form a part of the detailed description. The drawings show, by way of illustration, specific embodiments in which the invention may be practiced. These embodiments are also referred to herein as "examples." The following detailed description is not to be taken in a limiting sense, and the scope of the present invention is defined by the appended claims and their equivalents.

A lead assembly, catheter, or other medical device is inserted into an umbilical vein of a fetus or young child. The umbilical vein provides a pathway to the heart, through which a therapeutic device can be delivered. In an example, a lead assembly is implanted in an in utero procedure. In an example, the lead assembly allows for growth of the child or fetus, for example by including an expandable structure such as one or more looped portions or coiled portions. In an example, a pulse generator is coupled to a placenta and to the lead assembly. In an example, antiarrhythmia therapy is delivered before, during, and/or after the birthing process. In another example, a lead assembly is implanted in a child shortly after the child is born. After birth, the umbilical vein remains open (internally) for a period of time, during which time a lead assembly (or other device) can be inserted through the umbilical vein. The umbilical vein eventually occludes, typically approximately a week after birth.

Implanting a lead assembly through an umbilical vein can provide a number of advantages. In some examples, cardiac rhythm management therapy is delivered to high-risk fetuses. In an example, an electrode is positioned in or near the heart more quickly and/or easily via the umbilical vein than can be done surgically through a cardiac vein, such as through the superior vena cava. In some examples, an increased number of therapeutic combinations and/or options are available using an umbilical vein than are normally available through a surgically-accessed cardiac vein. In an example, a fetus is treated in utero and allowed to approach full term, and pre-term labor is avoided or reduced. In an example, an umbilically-implanted lead assembly is more compatible with fetal or infant growth than a lead assembly surgically inserted through a cardiac vein. In an example, a lead assembly and pulse generator is deliverable with an infant through normal birth, i.e. the devices are deliverable through the birth canal, or through a caesarian section. In an example, a device and lead is capable of delivering therapy during labor and birth. In an example, a lead assembly in an umbilical cord avoids risk of entanglement with a fetus because the lead assembly extends inside the umbilical cord. In an example, an umbilically-implanted lead assembly avoids or reduces the use or occlusion of permanent vessels in the peripheral vasculature. In an example, an umbilically-implanted lead assembly provides a bridge to adult and/or conventional cardiac rhythm management device, for example by allowing a child to grow until the cardiac and other anatomy can accommodate a subcutaneous device connected to a lead that is placed in, on, or around the heart through the peripheral vasculature.

Figure 2:
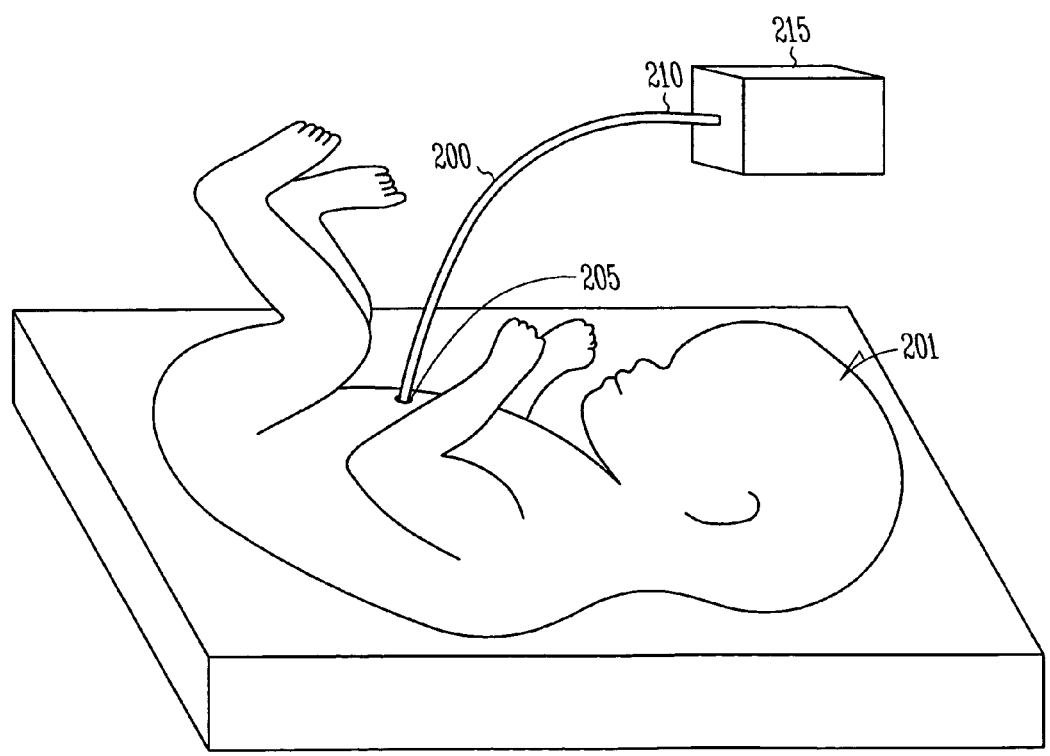
FIG. 2 is an illustration of a child patient and a lead assembly inserted through a catheterized umbilicus.
Figure 3:
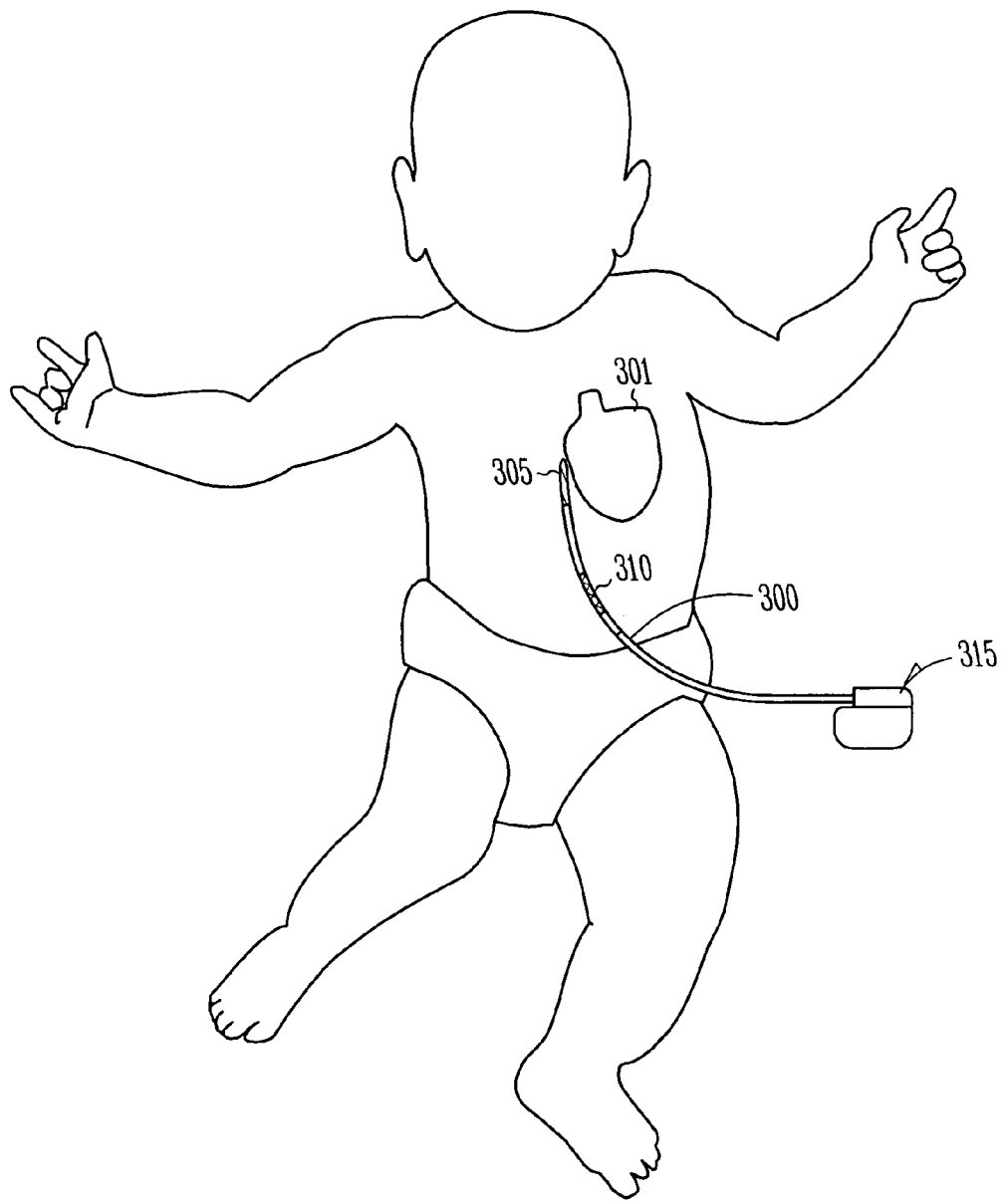
FIG. 3 is an illustration of a patient and a lead assembly extending from a medical device through an umbilical vein toward the patient's heart.
Figure 4:
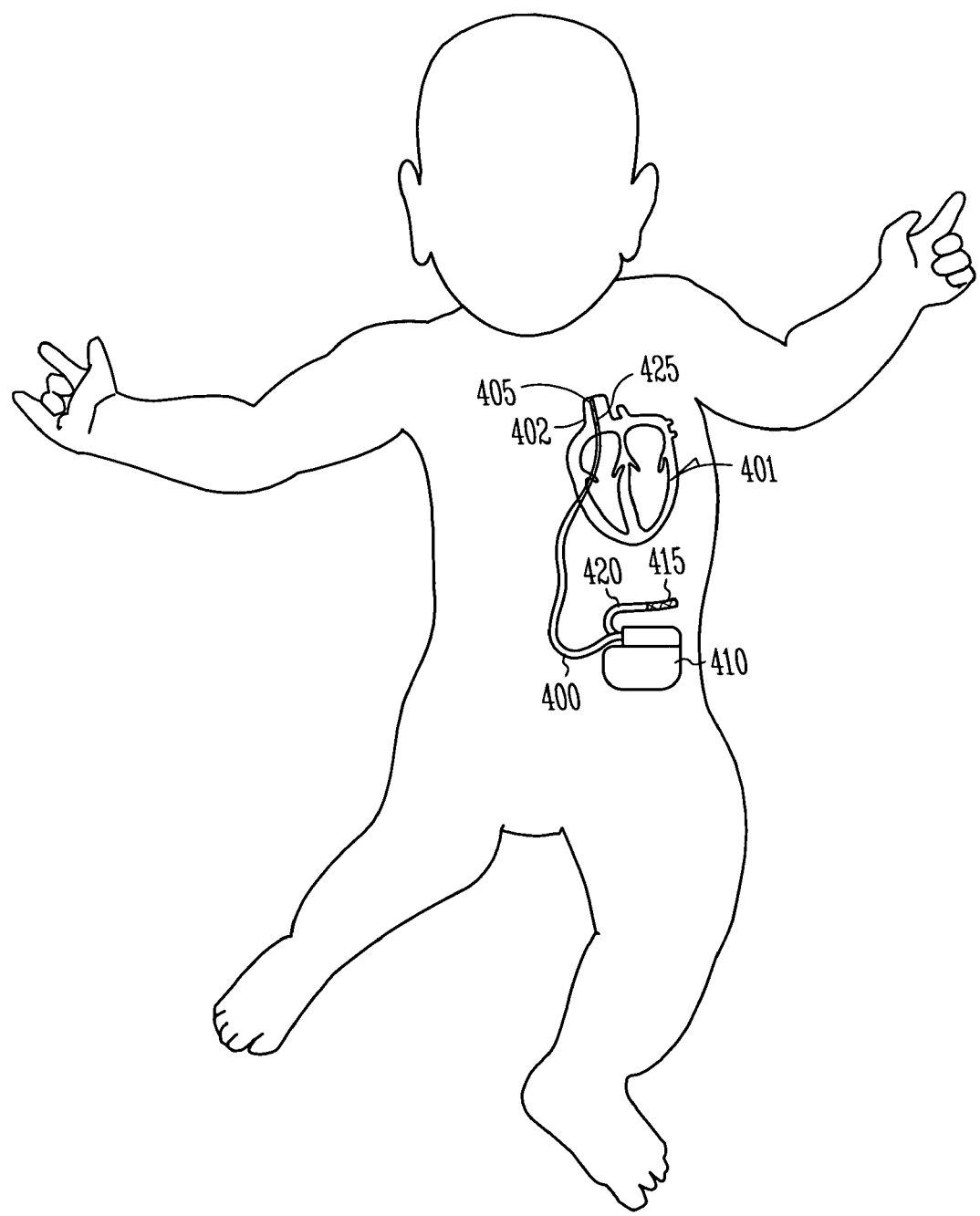
FIG. 4 is an illustration of a patient, a first lead assembly extending from a medical device into a patient's heart, and a second lead assembly extending into or onto the patient.
Figure 5:
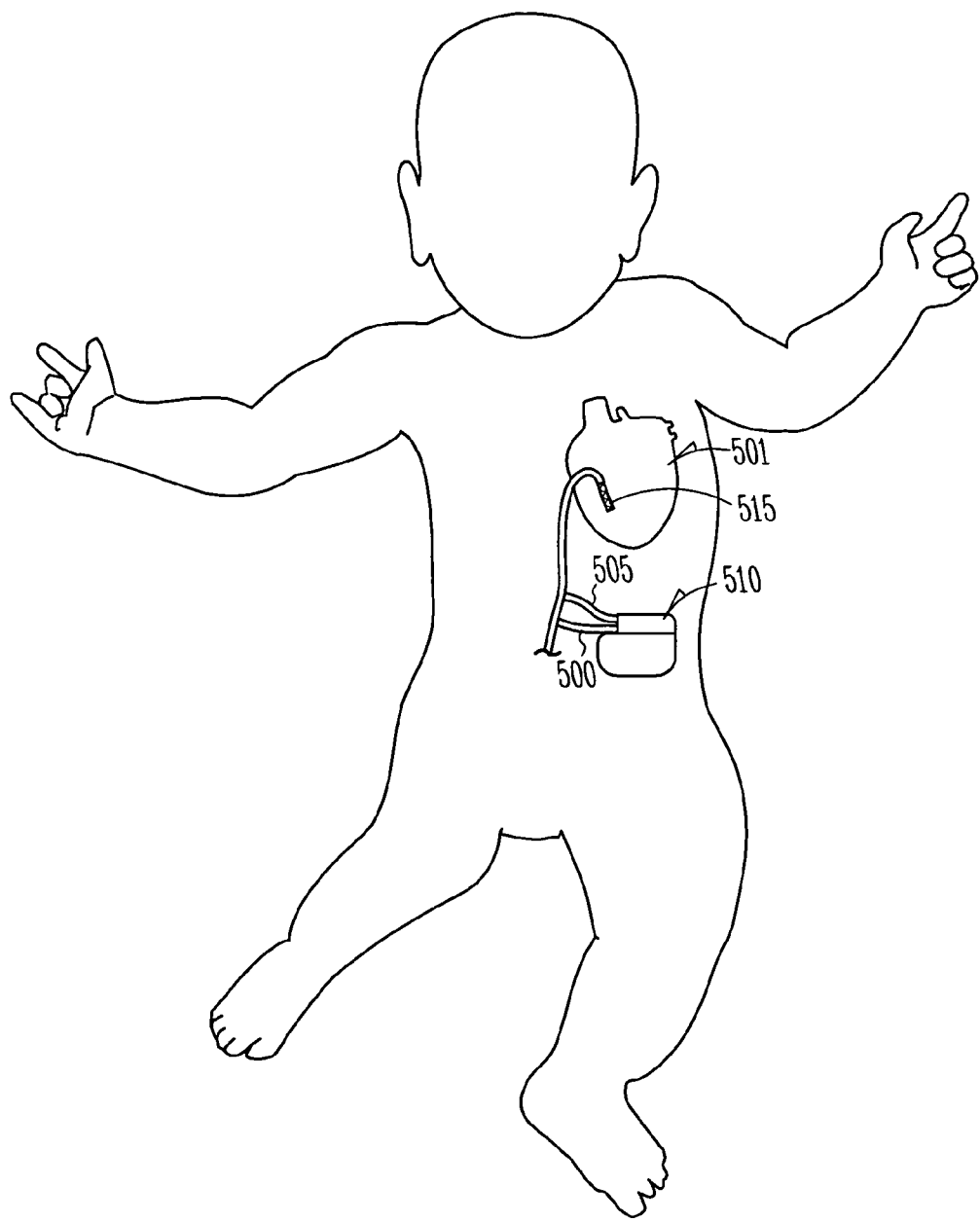
FIG. 5 is an illustration of a patient, a first lead assembly extending from a patient toward the patient's heart, and a second lead assembly inserted into the patient's inferior vena cava.
Figure 9:
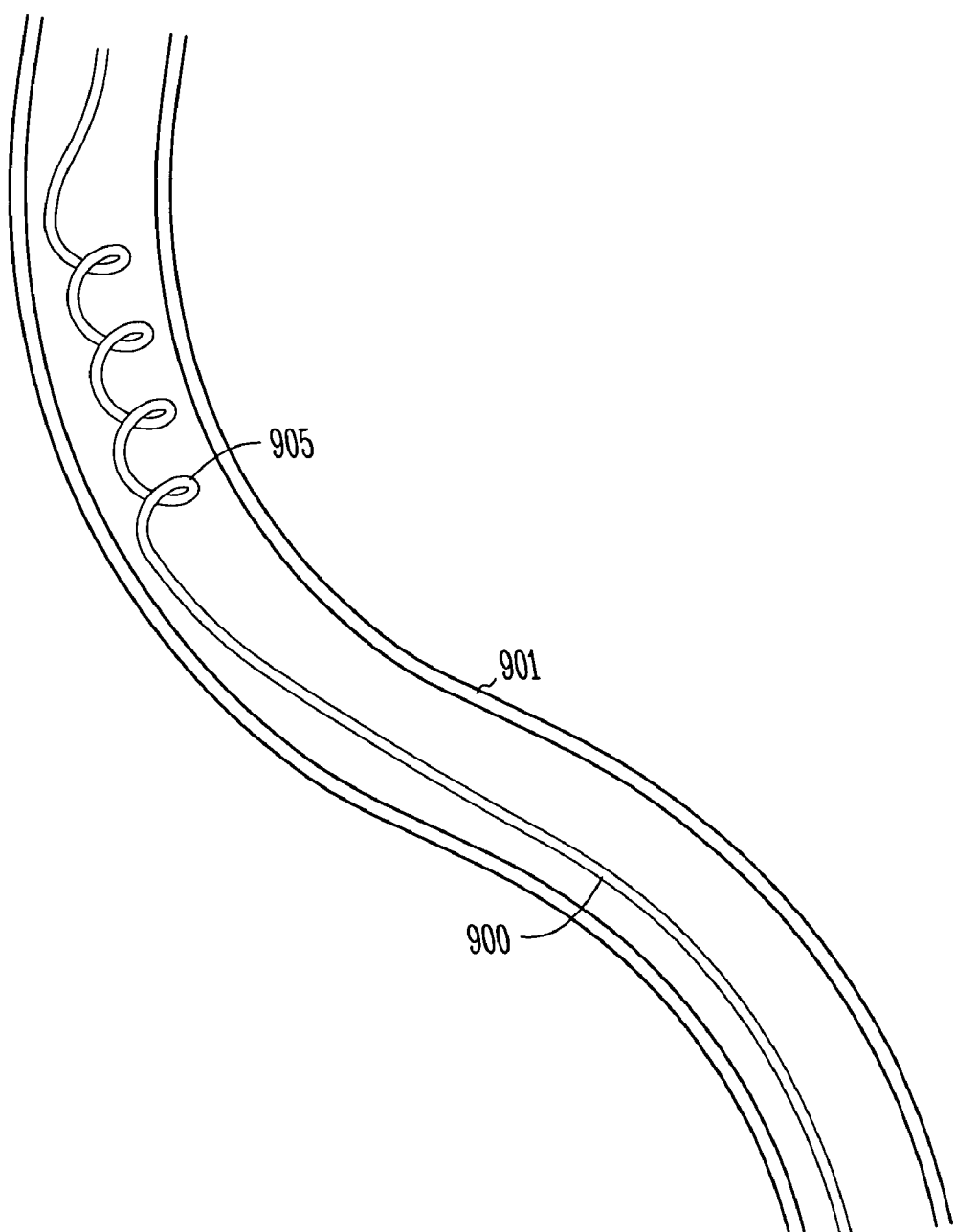
FIG. 9 is illustration of a lead assembly in a blood vessel.
Figure 10:
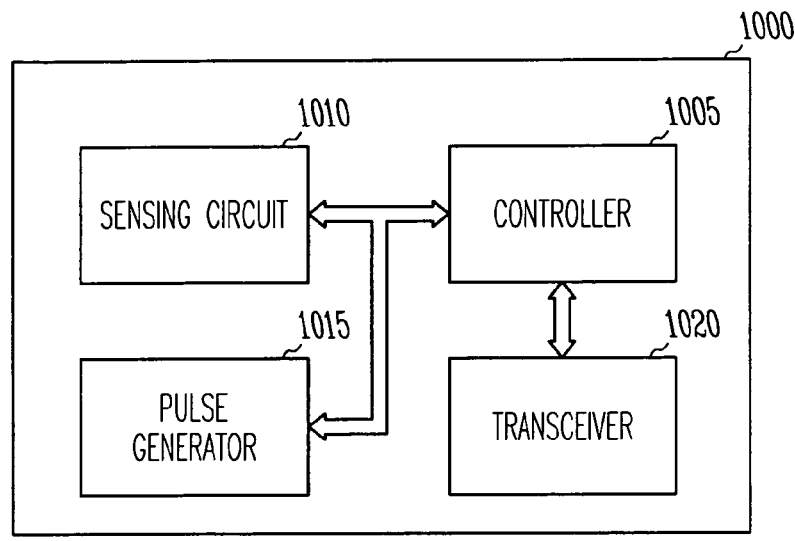
FIG. 10 is a schematic illustration of an implantable medical device.
Figure 11:
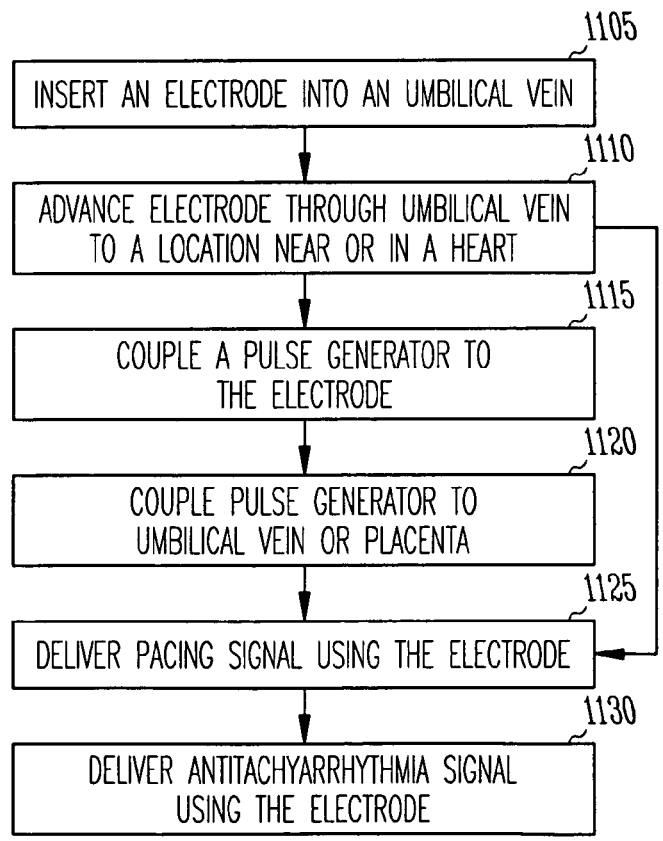
FIGS. 11 and 12 are flow charts that illustrate example methods.
Figure 12:
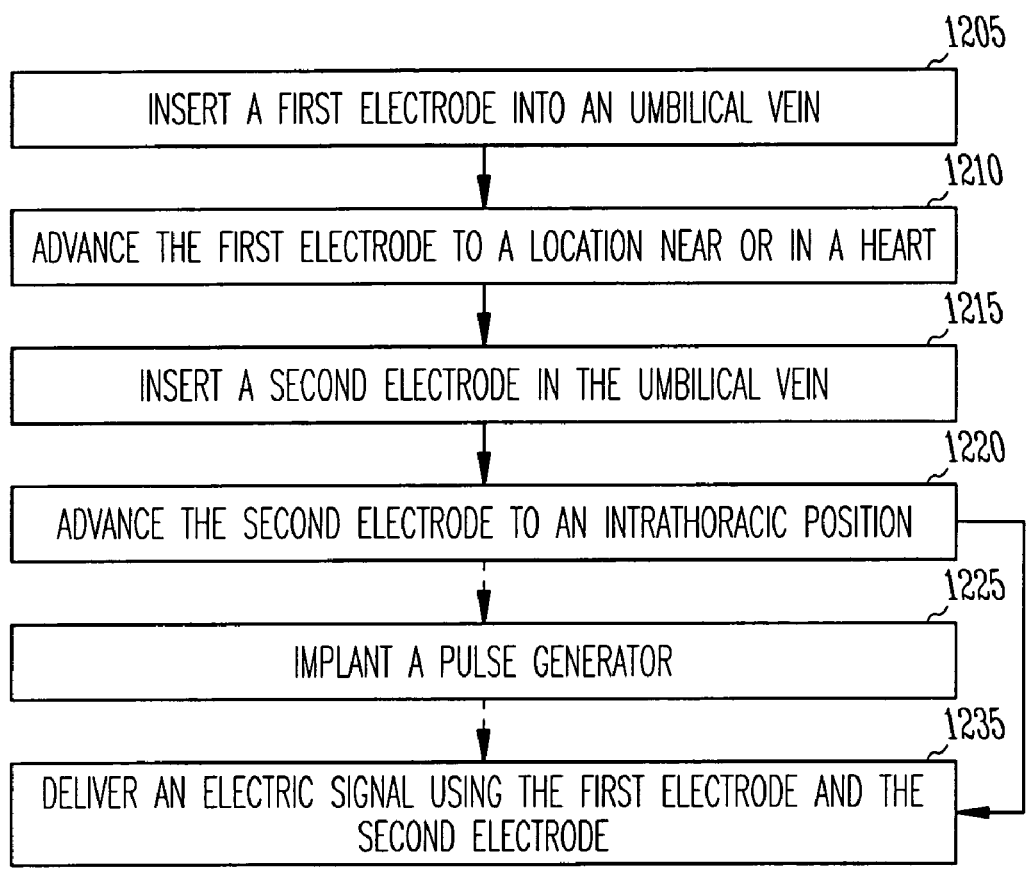

Various example techniques include inserting a lead assembly or other device through the umbilical vein. In an example, a pacing therapy is delivered through an umbilically-implanted lead assembly. In another example, a defibrillation therapy or other antitachyarrhythmia therapy is delivered using multiple electrodes on a lead assembly, electrodes on separate lead assemblies, or an electrode on a lead assembly and an electrode coupled to a medical device housing or "can." FIG. 1 shows an example where a lead assembly is inserted into an umbilical vein in utero and a pulse generator is connected to a placenta. FIG. 2 illustrates another example in which a lead assembly extends through a catheterized umbilicus. FIGS. 3-5 show various configurations of lead assemblies in a fetus or infant. FIGS. 6, 7, and 8A-D show internal anatomy and lead assemblies extending through an umbilical vein and other anatomy. FIG. 9 shows a lead assembly extending through a vessel and having slack that allows the lead assembly to expand in length as an infant or fetus grows. FIG. 10 is a schematic illustration of a medical device including controller circuitry. FIGS. 11 and 12 are flowcharts that illustrate example methods.

Turning now to FIG. 1, a lead assembly 100 extends into an umbilical vein 105 of an in utero fetus 110 and a placenta 120. A pulse generator 115 is coupled to the placenta 120. In an example, the pulse generator is sutured to the placenta at a location that does not significantly compromise blood flow or result in the loss of blood. Alternatively, a fabric pouch is sutured or stapled to the placenta, and the pulse generator is placed in the pouch. In another example, a pouch is dissected into a wall of the placenta in a manner similar to typical subcutaneous implantation. In an example, a wall 125 of the umbilical vein 105 is perforated, and the lead assembly is inserted into the umbilical vein. The umbilical vein 105 extends from the placenta 120 to the fetus 110. Inside the fetus, the umbilical vein 105 extends through the abdomen and thorax to the heart. In an example, the lead assembly and/or pulse generator are placed in a surgical procedure, optionally using direct visualization by the implanter. Optionally, imaging technology, such as ultrasound, X-ray, magnetic resonance imaging (MRI), computerized axial tomography (CT or CAT scan), endoscopic technology or a combination thereof, is used to assist with positioning and placement of the lead assembly and/or pulse generator. In an example, techniques used to perform one or more of amniocentesis, spina bifida surgery, mesh stent placement for fetal urinary obstruction, fetoscopic techniques for tumor removal, caesarian-section delivery, and/or modifications thereof are used in a procedure to implant a lead assembly in an umbilical vein. In an example, the lead assembly 100 includes one or more electrodes for delivering pacing, defibrillation, or other therapy.

Referring now to FIG. 2, in another example, a lead assembly 200 extends into an umbilical vein in a young child 201. In an example, an umbilicus is catheterized within about a week of birth, and a lead assembly is inserted through the umbilicus 205 into the umbilical vein. Alternatively, a lead assembly is inserted into the umbilical vein through the abdomen in a surgical procedure. In an example, a distal end of the lead assembly is inserted through the umbilical vein and other anatomy and positioned in or near the heart, where electrodes can sense intrinsic electrical heart signals or other parameters, and/or deliver antiarrhythmia therapy such as pacing or defibrillation. In an example, a proximal end 210 of the lead assembly is coupled to an external medical device 215 that records and/or analyzes detected physiological data, and/or delivers antiarrhythmia therapy through electrodes on the lead assembly. Alternatively, a lead assembly is coupled to an implanted medical device. A schematic illustration of an implantable medical device is shown in FIG. 10.

FIG. 3 is an illustration of a lead assembly 300 and a heart 301 of a fetus or young child. The lead assembly 300 includes first and second defibrillation electrodes 305, 310. A distal end portion of the lead assembly 300 extends near the heart 301. In an example, the first defibrillation electrode 305 is positioned in the inferior vena cava. In an example, the second defibrillation electrode 310 is positioned in the inferior vena cava spaced a distance below the first defibrillation electrode 305. In another example, the second defibrillation electrode 310 is positioned in the umbilical vein or elsewhere in the abdomen. An antitachyarrhythmia therapy, such as a defibrillation therapy, is deliverable through the first and second electrodes 305, 310. In an example, the first and second defibrillation electrodes 305, 310 are positioned to create a defibrillating electric field across the heart. In an example, the lead assembly 300 is electrically coupled to a device 315, such as pulse generator. The device 315 is optionally but not necessarily implantable. In an example, the device includes a circuit to generate a therapeutic electric pulse that is deliverable through the defibrillation electrodes. The device 315 additionally or alternatively includes analysis circuitry to determine when an antitachyarrhythmia therapy or other therapy is needed. In an example, the lead assembly 300 includes one or more pacing and/or sensing electrodes, and the device 315 also includes pacing circuitry.

FIG. 4 is an illustration of a lead assembly 400 extending into a heart 401 of a fetus or young child. In an example, the lead assembly extends through the umbilical vein, through the inferior vena cava, into the heart 401, and into the superior vena cava (SVC) 402. In an example, a portion 425 of the lead assembly 400 situated in the SVC 402 includes an electrode 405, such as a defibrillation electrode. In an example, the lead assembly 400 is surgically inserted into the umbilical vein at a location in the abdomen. Alternatively, the lead assembly 400 extends into the umbilical vein through a catheterized umbilicus. In an example, the lead assembly 400 is electrically coupled to a medical device 410, which is optionally implanted in the fetus or young child. In another option, the medical device 410 is connected to a placenta in the treatment of a fetus. The medical device 410 includes circuitry such as pulse generation circuitry and/or analysis circuitry.

In an example, the medical device 410 is implanted in a left thoracic location, such as a left side of the abdomen. In an example, a second electrode 415 is coupled to the device 410. In an example, a second lead assembly 420 includes the second electrode 415 and couples the electrode to the medical device 410. In an example, the second electrode 415 is positioned superior to the device 410. In an example, the second electrode 415 is positioned at a location that is below the heart 401 when the infant is in a vertical (i.e. standing) position. In another option, the electrode is connected directly to the medical device, and the second lead assembly 420 is optionally omitted. An antitachyarrhythmia therapy is deliverable through the electrodes 405, 415. In an example, an electrical field generated by the electrode is sufficient to defibrillate a majority or all of the heart 401.

FIG. 5 shows another example in which first and second lead assemblies 500, 505 extend into a vessel on or near the heart 501, such as the inferior vena cava. In an example, the first lead assembly 500 includes a pacing electrode 515 and the second lead assembly 505 includes one or more defibrillation electrodes. In an example, the first lead assembly 500 extends into the heart 501. In an example, a pacing electrode on the second lead assembly is positioned in the heart, such as in the right ventricle, for example. In an example, one or both of the lead assemblies 500, 505 are surgically inserted into the umbilical vein at a location in the abdomen. Alternatively, one or both of the lead assemblies are inserted through a catheterized umbilicus into the umbilical vein. In an example, the lead assemblies are coupled to a medical device 510, which is optionally implanted in an abdomen in a fetus or child, or connected to a placenta. In an example, the medical device 510 includes circuitry to analyze detected physiological data and/or deliver an antiarrhythmia therapy such as pacing or defibrillation.

Figure 6:
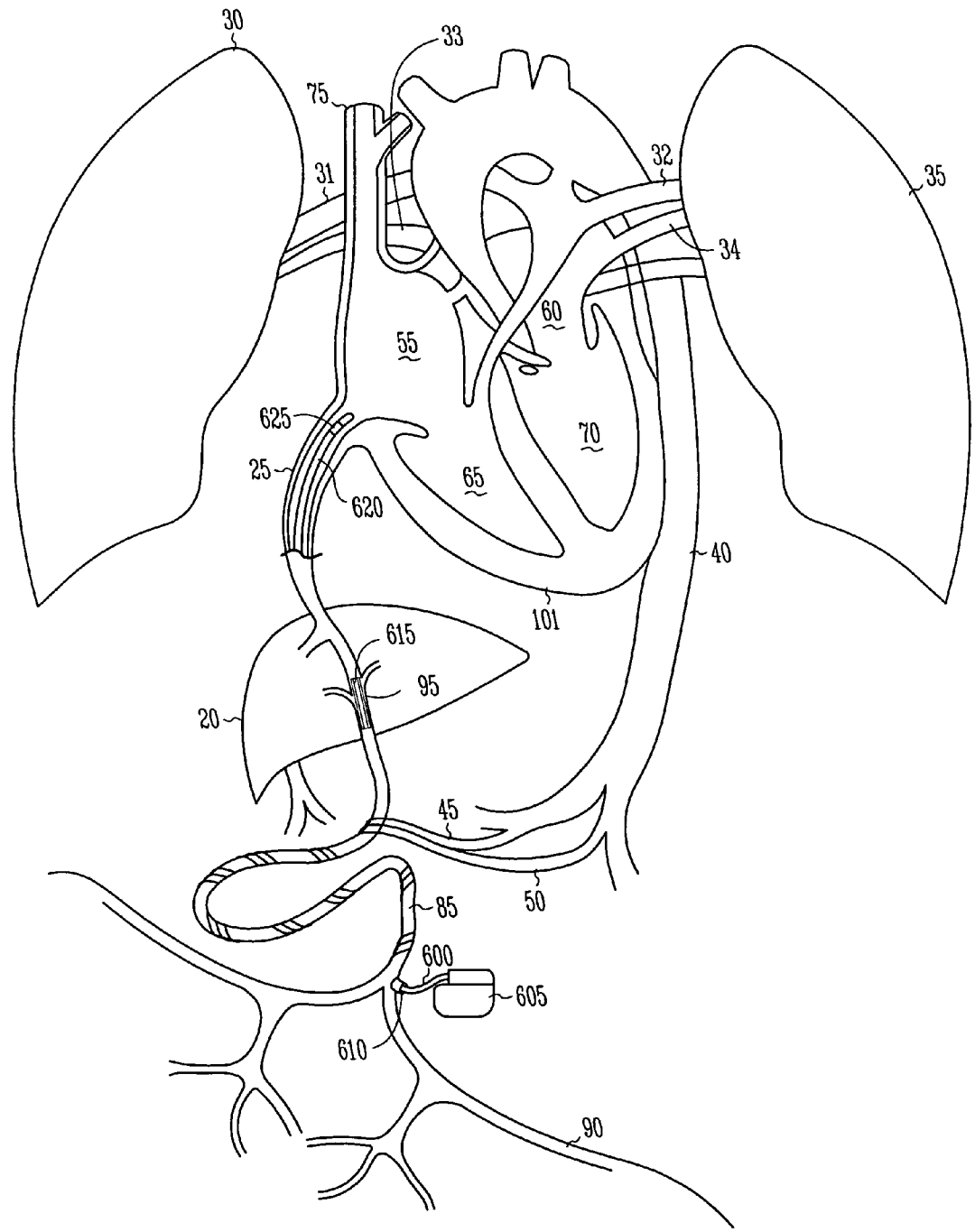
FIG. 6 is an illustration of internal organs, vasculature, an umbilical vein, a placenta, and a lead assembly extending from a medical device into the umbilical vein and toward the heart.
Figure 7:
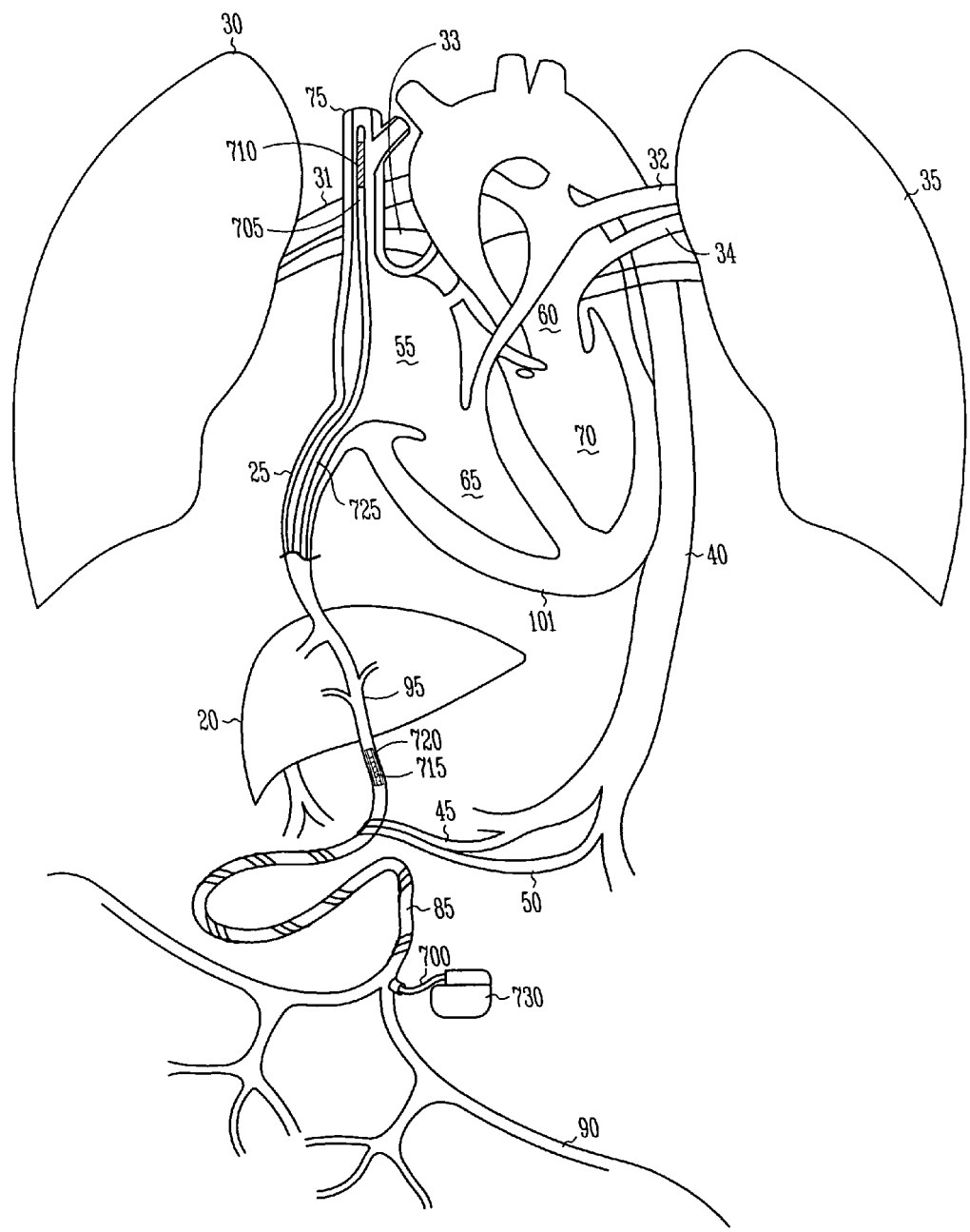
FIG. 7 is an illustration of internal organs, vasculature, an umbilical vein, a placenta, and a lead assembly extending from a medical device into the umbilical vein and into the heart.
Figure 8A:
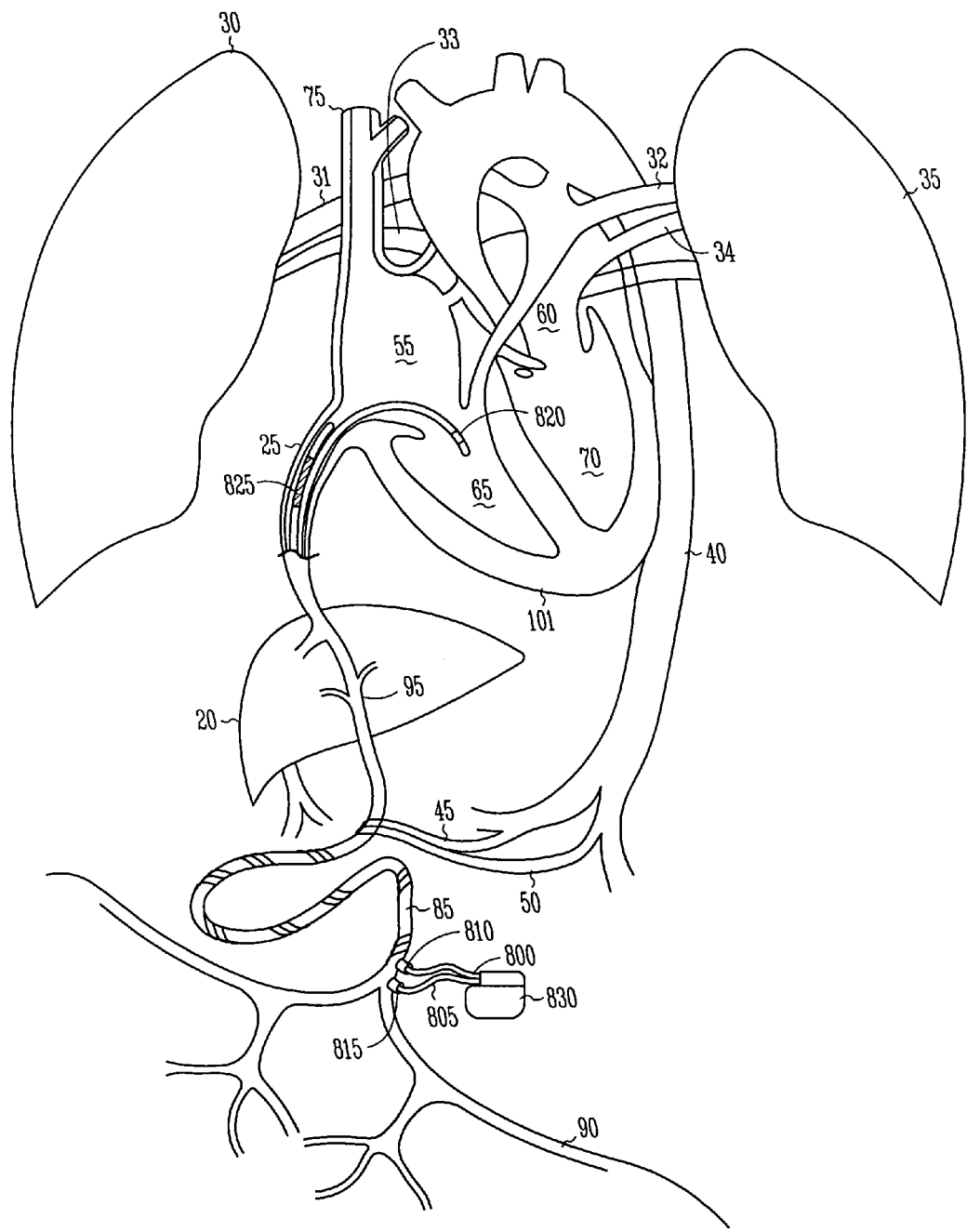
FIG. 8A is an illustration of internal organs and vasculature, an umbilical vein, a placenta, a first lead assembly extending from a medical device into the umbilical vein and toward the heart, and a second lead assembly extending from a medical device into the umbilical vein and into the heart.

FIGS. 6, 7, and 8A show lead assemblies and various anatomical features. An umbilical vein 85 extends from a placenta 90 to the ductus venous 95 and liver 20. The ductus venous 95 connects with the inferior vena cava 25 and carries blood to the heart 101. FIGS. 6, 7, and 8A also show the lungs 30, 35, pulmonary arteries 31, 32, pulmonary veins 33, 34, aorta 40, and umbilical arteries 45, 50. The right and left atria 55, 60, right and left ventricles, 65, 70, and superior vena cava (SVC) 75 are also shown. The umbilicus is not shown, but it is understood that the umbilical vein extends through the umbilicus in a fetus.

Referring now to FIG. 6 a lead assembly 600 extends from a medical device 605 into the umbilical vein 85 and toward the heart 101. In an example, the lead assembly is inserted into a portion of the umbilical vein extending between the placenta 90 and a fetus. In an example, a suture sleeve 610 and sutures are used at the location where the lead assembly 600 enters the umbilical vein 85 to seal and/or stabilize the vein. In an example, extending the lead assembly 600 through the umbilical vein 85 avoids the presence of a loose lead assembly in the womb and avoids potential complications associated therewith. Alternatively, the lead assembly 600 is inserted into the placenta and then into the umbilical vein. In another example, the lead assembly is inserted through a catheterized umbilicus of a fetus or young child. In another example, the lead assembly is surgically implanted in the abdomen and inserted into the umbilical vein.

Referring again to FIG. 6, in an example, the lead assembly 600 extends through the umbilical vein 85 and venous ductus 95, and into the inferior vena cava 25. Portions of anatomy are shown cut away in FIG. 6 to reveal a portion 615 of the lead assembly 600 extending through the venous ductus and another portion 620 of the lead assembly extending through the inferior vena cava. In an example, the lead assembly includes a pacing electrode 625 near the heart 101. In another example, the lead assembly 600 additionally or alternatively includes one or more defibrillation electrodes, as shown in FIG. 3, for example. In an example, fetoscopic techniques such as MRI techniques or ultrasound or the like are used to facilitate positioning of a lead assembly. The medical device 605 optionally is connected to the placenta 90, for example by sutures. In an example, the medical device includes a pulse generating circuitry and/or analysis circuitry, as shown in FIG. 10, for example. In an example, the medical device determines an antiarrhythmia therapy, such as a pacing or defibrillation therapy, and delivers the therapy using one or more electrodes on the lead assembly 600.

Referring now to FIG. 7, in another example, a lead assembly 700 extends into the umbilical vein 85, through the venous ductus 95, through the inferior vena cava 25, into the right atrium 55 of the heart 101, and into the superior vena cava (SVC) 75. In an example, a portion 705 of the lead assembly 700 positioned in the SVC includes an electrode 710, such as a defibrillation electrode. In an example, a second defibrillation electrode 715 is positioned elsewhere on the lead assembly 700, such as on a portion 720 of the lead assembly positioned in the umbilical vein 85. Alternatively, the second electrode is positioned in another location, such as on a portion 725 of the lead assembly in the IVC. In another example, an electrode is positioned between the SVC and the heart or between the IVC and the heart. In another example, the lead assembly 700 includes three or more defibrillation electrodes. An antitachyarrhythmia therapy such as a defibrillation therapy is deliverable using the first and second defibrillation electrodes 710, 715. In an example, a pulse generator in the medical device 730 provides a defibrillation energy that is delivered using the electrodes 710, 715. In an example, the therapy delivers a defibrillation energy that generates a defibrillating electric field over most or all of the heart.

Figure 8B:
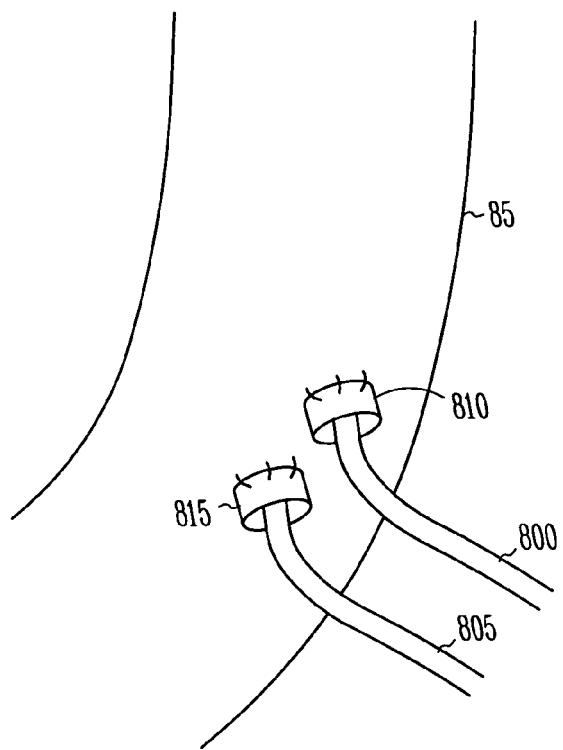
FIG. 8B is an enlarged view of a portion of FIG. 8A showing the first and second lead assemblies extending into the umbilical vein.
Figure 8C:
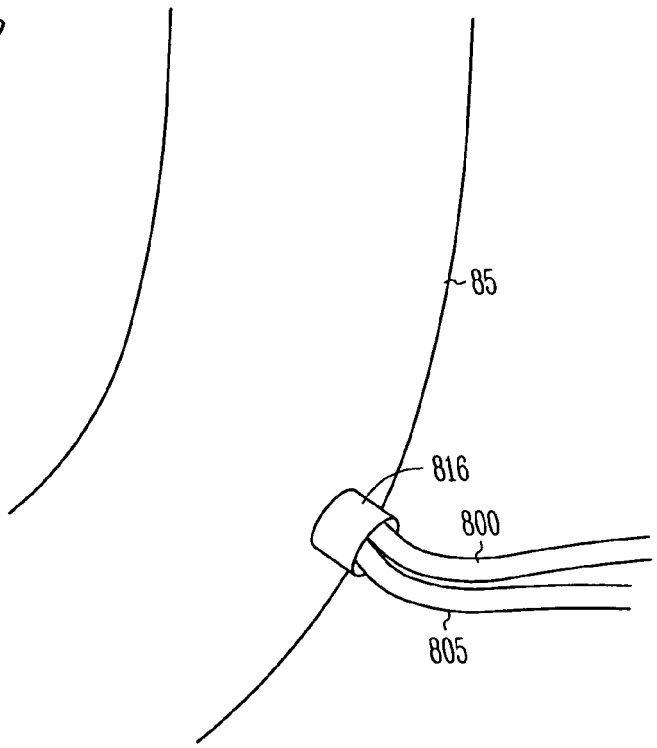
FIG. 8C is an enlarged view of an alternate configuration in which the first and second lead assemblies extending into a single suture sleeve and then into the umbilical vein.
Figure 8D:
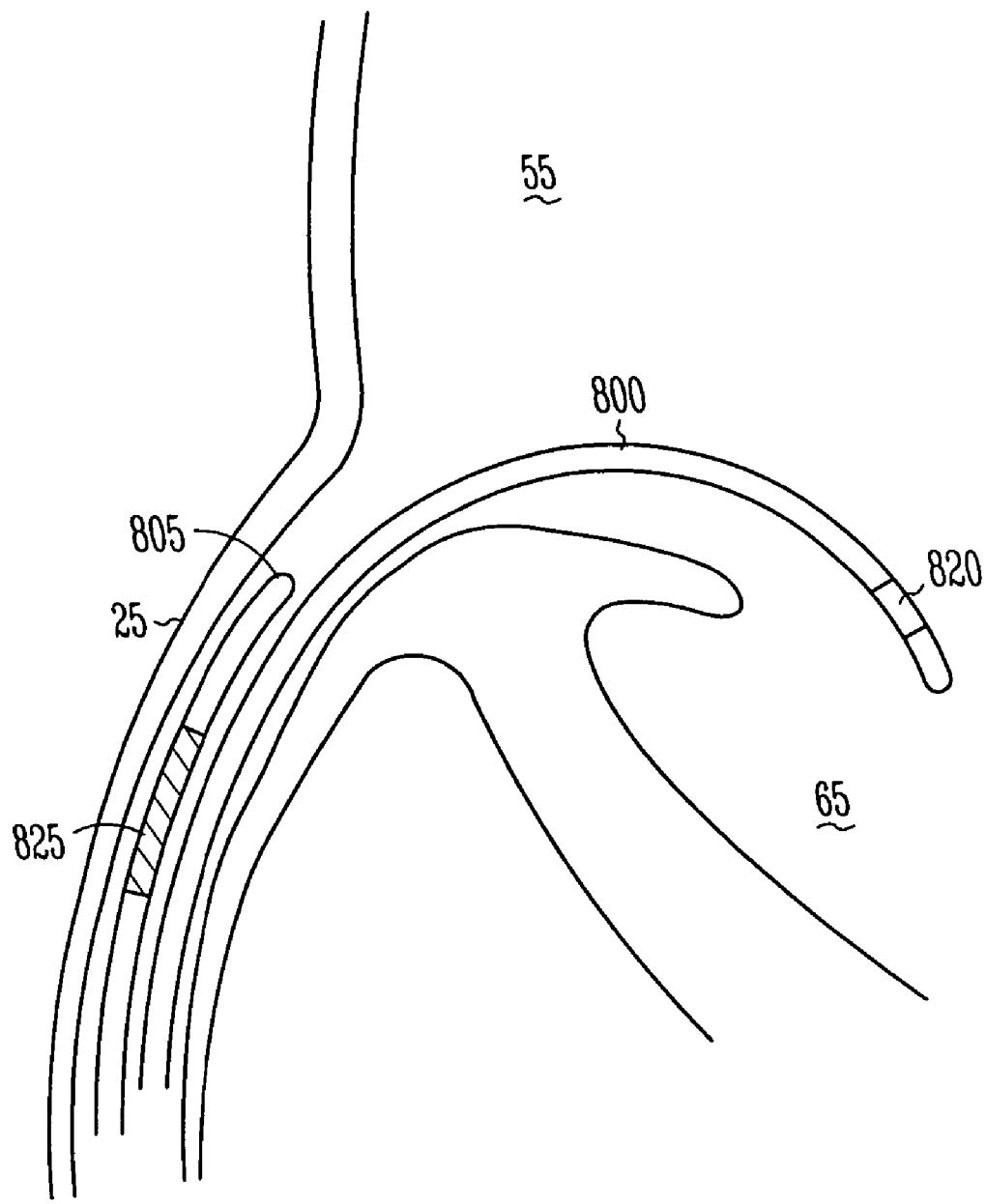
FIG. 8D is an enlarged view of a portion of FIG. 8A showing the first lead assembly approaching but not entering the heart and the second lead assembly extending into the heart.

Referring now to FIGS. 8A-D, in another example configuration, two lead assemblies 800, 805 extend into an umbilical vein 85. In an example, the lead assemblies 800, 805 extend into separate suture sleeves 810, 815. FIG. 8B shows an enlarged view showing the suture sleeves 810, 815 and sutures. In an alternative, both lead assemblies 800, 805 extend into a single suture sleeve 816, as shown in FIG. 8C. In an example, the first lead assembly 800 extends into the heart 101, and the second lead assembly 805 extends into the inferior vena cava 25 but does not extend into the heart. FIG. 8D shows an enlarged view of the lead assemblies 800, 805, the IVC 25, and a portion of the heart. Alternatively, the second lead assembly extends into the heart and optionally into the superior vena cava 75, as shown in FIG. 8A. In an example, the first lead assembly 800 is fixated in the heart and includes a pacing electrode 820. In an example, the second lead assembly 805 includes at least one defibrillation electrode 825. In an example, one of the first or second lead assemblies 800, 805 includes one or more additional electrodes. In an example, the lead assemblies 800, 805 are coupled to a medical device 830 including pulse-generating circuitry and optionally including one or more defibrillation electrodes. An antitachyarrhythmia therapy is deliverable using the electrodes.

While the FIGS. 6, 7, and 8A show fetal anatomy, it is understood that the configurations shown and described, and variations thereof, can also be employed with children before, during, or after the anatomy changes from fetal to post-partum configurations. For example, after birth but before the umbilical vein collapses and/or occludes, the lead assembly can be inserted through the umbilicus and advanced toward the heart through the umbilical vein. A lead assembly inserted into an umbilical vein before the vein degrades and/or occludes can be used after the degradation/occlusion to deliver antiarrhythmia therapies.

In an example, slack is provided in the lead assembly, so that the lead assembly can slide and/or expand in the umbilical vein as the fetus/child and umbilical vein grow in length. FIG. 9 is illustrates an example lead assembly 900 in a blood vessel 901. In an example, the lead assembly includes a coiled portion 905 that is extendable. In an example, the outer diameter of the coiled portion 905 is smaller than the inner diameter of the portion(s) of the umbilical vein in which the coiled portion is located. In an example, the pitch of the coiled portion gets larger as the child/fetus grows. In an example, multiple coiled portions are provided on the lead assembly. In another example, a loop is provided instead of a coil. The loop tightens (reduces in radius) to provide additional length and allow growth. In another alternative, a slip suture sleeve is provided. The slip suture sleeve allows the lead assembly to slip through the sleeve to accommodate growth of the fetus/child.

In an example, a lead assembly includes a coating that prevents tissue ingrowth. In an example, a coating such as ePTFE is provided on the lead assembly to prevent tissue ingrowth. In another example, a drug eluting coating is provided on the lead assembly.

FIG. 10 is a schematic illustration of an implantable medical device 1000. The device 1000 includes a controller 1005 that is communicatively coupled to a sensing circuit 1010 and a pulse generator 1015. In an example, the controller 1005 receives data from the sensing circuit 1010 that is indicative of one or more physiological parameters in a patient. In an example, the controller 1005 analyzes the data provided by the sensing circuit 1010 and determines a therapy, such as a pacing or defibrillation therapy. In an example, the controller 1005 instructs the pulse generator 1015 to deliver a therapy, such as a pacing or defibrillation signal. In an example, the controller is also communicatively coupled to a transceiver 1020. In an example, the controller communicates with an external programmer through the transceiver 1020. In another example, the controller 1005 communicates with an external module, such as an implanted sensing or therapy module through the transceiver 1020. In an example, the transceiver 1020 communicates through radio frequency (RF) signals or through conduction through the body. In an example, the controller 1005, sensing circuit 1010, pulse generator 1015 and transceiver 1020 are all contained in a single module. In another example, the sensing circuit 1010 and/or pulse generator 1015 are contained in different module that is physically separate from a first module that includes the controller. In an example, the sensing circuit and/or pulse generator are coupled to a transceiver that communicates with the controller through the transceiver 1020. In an example, a module is implanted using a lead assembly, catheter or other device that is extended through the umbilical vein.

FIG. 11 schematically illustrates an example method. At 1105, an electrode is inserted into an umbilical vein. In an example, a fetus or child is sedated or anesthetized before the electrode is inserted. At 1110, the electrode is advanced though the umbilical vein to a location near or in a heart. The electrode is optionally inserted in utero. In an example, the insertion procedure uses surgical techniques developed to perform, for example, amniocentesis, spina bifida surgery, mesh stent placement for fetal urinary obstruction, fetoscopic techniques for tumor removal, or caesarian-section delivery, or modifications thereof. Alternatively, the electrode is inserted after birth, for example by catheterizing the umbilicus or through a surgical procedure in the abdomen. In an example, a lead assembly is inserted into the umbilical vein, and the lead assembly includes the electrode. In an example, slack is provided in the lead assembly. In an example, providing slack allows fetal growth, maternal growth, and/or natural fetus movement. In an example, providing slack includes providing a coiled portion. In an example, a suture sleeve is positioned at a location where the lead assembly exits the umbilical vein, and the vein is sutured, for example, using a purse string suture. In an example, the suture sleeve and suture stabilizes the lead assembly exit site. In an example, the lead assembly is coupled or anchored to the umbilical vein at one or more locations. In an example, attaching the lead assembly to the vein is connected to an internal surface of the umbilical vein. In another example, the lead assembly is connected to an external surface of the umbilical vein. In an example, the lead is attached to the heart to avoid dislodgment, for example using an active fixation electrode.

Referring again to FIG. 11, at 1115, a pulse generator is optionally coupled to the electrode. In an example, the pulse generator is coupled to a lead assembly that is coupled to the electrode. At 1120, the pulse generator is optionally coupled to an umbilical vein or a placenta. Alternatively, the pulse generator is coupled to a maternal anatomical location, such as a location in the uterus or abdomen. In another example, a pulse generator is implanted subcutaneously in the patient's thorax. At 1125, a pacing signal is delivered using the electrode. In an example, a unipolar pacing lead is used. In an example, a pacing signal is delivered using an electrode on a unipolar lead and an electrode on a pulse generator casing. At 1130, an antitachyarrhythmia signal is delivered using the electrode. In an example, an antitachyarrhythmia is delivered using the electrode, but a pacing signal is not delivered using the electrode (i.e. operation 1125 is omitted.) In another example, a pacing signal is delivered, but an antitachyarrhythmia signal is not delivered.

Referring now to FIG. 12, another example method is schematically illustrated. At 1205, a first electrode is inserted into an umbilical vein. In an example, the first electrode is a defibrillation electrode. At 1210, the first electrode is advanced to a location near or in a heart, such as the SVC. In an example, the first defibrillation electrode is advanced to a position that is near the heart but not in the heart. In an example, advancing the defibrillation electrode to a location in or near a heart includes positioning the electrode in the inferior vena cava (IVC). At 1215, a second defibrillation electrode is inserted in the umbilical vein. At 1220, the second umbilical electrode is advanced to an intrathoracic position. In an example, the second defibrillation electrode is advanced to a location in or near the abdomen. In an example, a lead assembly is inserted into the umbilical vein, and the lead assembly includes the first and second electrodes. In another example, a first lead assembly includes the first electrode and a second lead assembly includes the second electrode.

Referring again to FIG. 12, at 1225, a pulse generator is optionally implanted. In an example, implanting a pulse generator includes implanting the pulse generator in a left abdominal position. In an example, a lead assembly is coupled to the pulse generator and a portion of the lead assembly including the second defibrillation electrode is positioned superior to the pulse generator. In an example, a lead assembly is coupled to the pulse generator and a portion of the lead assembly including the second defibrillation electrode is positioned in an inferior vena cava (IVC). In an example, the lead assembly positioned in the IVC is a lead assembly with a slender lead body, such as a unipolar lead. At 1235, an electric signal such as a pacing signal or antitachyarrhythmia therapy signal is delivered using the first electrode and the second electrode. In an example, one electrode is an anode and the other is a cathode. In another example, a shock is delivered using three or more electrodes. In an example, an electrode is connected to a medical device casing.

While the methods, systems, and devices have been shown and described herein with respect to a human patient, it is understood that the methods, systems and devices can also be applied to animals, such as pigs or dogs, in therapeutic and/or experimental applications.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method comprising:
   inserting a first defibrillation electrode into an umbilical vein; and
   advancing the first defibrillation electrode to a location near a heart, but not in the heart.

2. The method of claim 1, further comprising inserting a second defibrillation electrode in the umbilical vein and advancing the second defibrillation electrode to an intrathoracic position.

3. The method of claim 2, wherein advancing the second defibrillation electrode to the intrathoracic position includes advancing the second defibrillation electrode to a location in or near the abdomen.

4. The method of claim 2, further comprising delivering an electrical signal using the first defibrillation electrode and the second defibrillation electrode.

5. The method of claim 2, wherein inserting the first defibrillation electrode into the umbilical vein and inserting the second defibrillation electrode in the umbilical vein include inserting a lead assembly into the umbilical vein, the lead assembly including the first defibrillation electrode and the second defibrillation electrode.

6. The method of claim 1, wherein advancing the first defibrillation electrode to the location near the heart, but not in the heart, includes advancing the first defibrillation electrode through the heart and into the superior vena cava (SVC).

7. The method of claim 1, wherein advancing the first defibrillation electrode to the location near the heart, but not in the heart, includes positioning the electrode in an inferior vena cava (IVC).

8. The method of claim 1, further comprising implanting a pulse generator, coupling the pulse generator to the first defibrillation electrode and a second defibrillation electrode, and delivering an electrical signal using the first defibrillation electrode and the second defibrillation electrode.

9. The method of claim 8, wherein implanting the pulse generator includes implanting the pulse generator in a left abdominal position.

10. The method of claim 8, further comprising inserting the second defibrillation electrode in the umbilical vein, wherein inserting the first and second defibrillation electrodes includes inserting a lead assembly including the first and second defibrillation electrodes into the umbilical vein; and coupling the lead assembly to the pulse generator and positioning a portion of the lead assembly including the second defibrillation electrode superior to the pulse generator.

11. The method of claim 8, further comprising inserting the second defibrillation electrode in the umbilical vein, wherein inserting the first and second defibrillation electrodes includes inserting a lead assembly including the first and second defibrillation electrodes into the umbilical vein; and coupling the lead assembly to the pulse generator and positioning a portion of the lead assembly including the second defibrillation electrode in an inferior vena cava (IVC).

12. The method of claim 1, wherein inserting the first defibrillation electrode into the umbilical vein includes inserting an electrode into a non-occluded umbilical vein.

13. A method comprising:

delivering an antiarrhythmia therapy using a lead assembly extending through an umbilical vein, including delivering the therapy in utero; and wherein the lead assembly includes a first defibrillation electrode and delivering the antiarrhythmia therapy includes delivering an antitachyarrhythmia therapy using the first defibrillation electrode.

14. The method of claim 13, wherein delivering the antiarrhythmia therapy using the lead assembly extending through the umbilical vein includes delivering the antiarrhythmia therapy through a lead assembly surgically implanted into the umbilical vein through an abdominal incision.

15. The method of claim 13, wherein delivering the antiarrhythmia therapy includes delivering the antiarrhythmia therapy using a first electrode on the lead assembly and a second electrode on a second lead assembly extending into an inferior vena cava.

16. A method comprising:

delivering an antiarrhythmia therapy using a lead assembly extending through an umbilical vein, including delivering the therapy in utero; and wherein delivering the antiarrhythmia therapy using the lead assembly extending through the umbilical vein further includes delivering an antiarrhythmia therapy through a catheterized umbilicus after birth.

17. The method of claim 16, wherein delivering the antiarrhythmia therapy through the catheterized umbilicus after birth includes delivering one or both of a pacing signal or an antitachyarrhytbmia signal using an electrode of the lead assembly positioned in or near a heart.

18. A method comprising:

inserting a lead assembly including an electrode into an umbilical vein, including inserting the electrode in utero:

advancing the lead assembly including the electrode through the umbilical vein to a location near or in a heart: and coupling a pulse generator to the lead assembly and securing the pulse generator to a placenta or the umbilical vein, and wherein securing the pulse generator to the placenta includes suturing the pulse generator to the placenta.

19. A method comprising:

inserting a lead assembly including an electrode into an umbilical vein, including inserting the electrode in utero:

advancing the lead assembly including the electrode through the umbilical vein to a location near or in a heart; and coupling a pulse generator to the lead assembly and securing the pulse generator to a placenta or the umbilical vein, and wherein securing the pulse generator to the placenta includes forming a placenta pouch and placing the pulse generator in the placenta pouch.

* * * * *

UNITED STATES PATENT AND TRADEMARK OFFICE
CERTIFICATE OF CORRECTION

PATENT NO.        : 7,551,959 B2
APPLICATION NO.   : 11/179121
DATED             : June 23, 2009
INVENTOR(S)       : Ronald W. Heil et al.

It is certified that error appears in the above-identified patent and that said Letters Patent is hereby corrected as shown below:

In column 12, line 12, in Claim 17, delete "antitachyarrhytbmia" and insert -- antitachyarrhythmia --, therefor.

In column 12, line 17, in Claim 18, delete "utero:" and insert -- utero; --, therefor.

In column 12, line 19, in Claim 18, delete "heart:" and insert -- heart; --, therefor.

In column 12, line 29, in Claim 19, delete "utero:" and insert -- utero; --, therefor.

Signed and Sealed this

Twenty-seventh Day of October, 2009

David J. Kappos
*Director of the United States Patent and Trademark Office*